US00PP29896P3

(12) United States Plant Patent
Hansen

(10) Patent No.: US PP29,896 P3
(45) Date of Patent: Nov. 27, 2018

(54) ***HIBISCUS* PLANT NAMED 'BALLET SLIPPERS'**

(50) Latin Name: ***Hibiscus* hybrid (L.)**
Varietal Denomination: Ballet Slippers

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 68 days.

(21) Appl. No.: 15/530,029

(22) Filed: Nov. 21, 2016

(65) Prior Publication Data

US 2018/0146587 P1 May 24, 2018

(51) Int. Cl.
*A01H 5/02* (2018.01)

(52) U.S. Cl.
USPC ..... Plt./257
CPC ..... *A01H 5/02* (2013.01)

(58) Field of Classification Search
USPC ..... Plt./257
CPC ..... A01H 5/02; A01H 5/00; A01H 6/608
See application file for complete search history.

(56) References Cited

PUBLICATIONS

Greenhouse Management Supplement Aug. 2016 New Perennial Varieties, retrieved on Nov. 8, 2017, retrieved from the Internet at https://www.greenhousemag.com/fileuploads/file/august2016_npvd.pdf, pp. 1-43 (Year: 2016).*

* cited by examiner

*Primary Examiner* — June Hwu

(57) ABSTRACT

A new and distinct cultivar of winter-hardy, herbaceous, perennial, hybrid *Hibiscus* plant named 'Ballet Slippers' comprising a compact habit of multiple, well-branched, basal stems over a prolonged season having a white middle portion, a shiny deep-red eye, blushed with pink along the petal tips and leading edges. Flower shape is slightly cupped with the leading petal edge slightly ruffled and not lying flat on the petal underneath. The foliage is three-lobed, deeply dissected, and dark green colored.

1 Drawing Sheet

Botanical classification: *Hibiscus* hybrid (L.).
Variety denomination: 'Ballet Slippers'.

BACKGROUND AND ORIGIN OF THE PLANT

The present invention relates to the new and distinct hardy, herbaceous, *hibiscus* plant, *Hibiscus* 'Ballet Slippers' hybridized under direction of the inventor on Jul. 25, 2012 at a nursery in Zeeland, Mich. The new plant is a single seedling selection from a cross between a proprietary unreleased *hibiscus* known by the breeder code 7-100-4 times a proprietary unreleased *hibiscus* known by the breeder code 11-SRF-225. The seeds were harvested in the fall of 2012 and the specific seedling passed the initial trial in the summer of 2014 at which time it was assigned the breeder code labeled # 12-99-13. Both parents have a complex mixture of species in them, most likely comprising the species: *moscheutos* and *coccineus*. *Hibiscus* 'Ballet Slippers' was first asexually propagated in 2014 by sterile shoot-tip tissue culture at the same nursery in Zeeland, Mich. The resultant asexually propagated plants have been found to be stable and true to type in successive generations of asexual reproduction.

No plants of *Hibiscus* 'Ballet Slippers' have been sold, either in this country or anywhere in the world, prior to the filing of this application, nor has any disclosure been made prior to the filing of this application with the exception of that which was within one year of the filing of this application and was derived directly or indirectly from the inventor.

BRIEF SUMMARY OF THE PLANT

*Hibiscus* 'Ballet Slippers' differs from its parents as well as all other hardy herbaceous *hibiscus* known to the applicant in many traits. The most similar *hibiscus* in flower color known to the applicant is *Hibiscus* 'Balhiblu' U.S. Plant Pat. No. 15,054.The habit of the new plant is taller and more floriferous and the petals more ruffled and less flat. The female parent is a solid darker pink and the habit was shorter than the new plant. Compared to the male parent, the new plant has flowers that are more white with light pink blushing toward the petal apex, and the habit is shorter and more compact.

*Hibiscus* 'Ballet Slippers' is a unique hardy herbaceous *hibiscus* with the following combined traits:

1. Winter-hardy, perennial with short compact habit of multiple, well-branched, basal stems.
2. Many rotate flowers over a prolonged season.
3. Flower petals having small red eye zone with a white middle portion and light pink blushing toward the apex.
4. Flower shape is slightly cupped with the leading edge or inside top edge of the petal slightly ruffled and not lying flat on the petal underneath.
5. Dark green, deeply-dissected, primarily tri-lobed foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
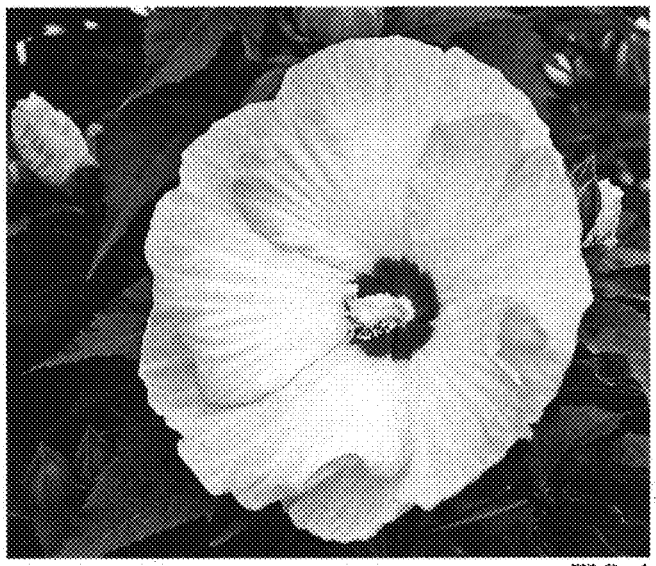
FIG. 1 shows a close-up of the flower.
Figure 2:
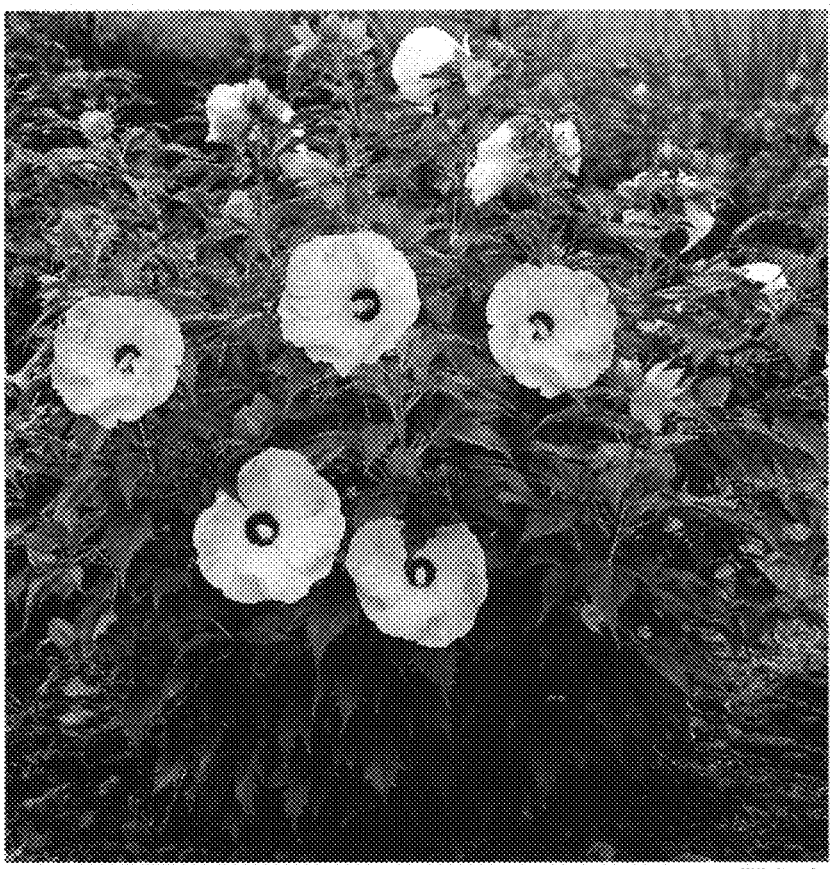
FIG. 2 shows the plant in full flower.

The following descriptions and color references are based on the 2001 edition of The Royal Horticultural Society Colour Chart except where common dictionary terms are used. The new plant, *Hibiscus* 'Ballet Slippers', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: A proprietary unreleased *hibiscus* known by the breeder code 7-100-4 (female seed parent) times *Hibiscus* 11-SRF-225 unreleased proprietary hybrid (male pollen parent);

Propagation:

*Method*.—Stem cuttings and sterile shoot-tip plant tissue culture division.

*Time to initiate roots from tissue culture*.—About two weeks.

*Rooting habit*.—Normal, branching, developing thick to about 3.0 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about 24 thick upright and heavily branched main stems producing a upright spreading mound to about 120.0 cm tall and about 120.0 cm wide; about 8 primary branches per main stem protruding at about 45° from horizontal; flowering from base to top of plant with up to about 58 flowers per main stem, average flowers per stem about 40.

*Stem*.—Terete, glabrous, glaucous; to about 120.0 cm tall and about 2.8 cm diameter at base, average about 110.0 cm tall and about 28.0 mm diameter at base.

*Stem color*.—Between RHS 144B and RHS 144A.

*Lateral branches*.—Average about 11 per stem; terete, glabrous, glaucous; to about 44.0 cm long and 9.0 mm diameter, average about 28.0 cm long and about 7.0 mm diameter.

*Lateral branch color*.—Between RHS 144B and RHS 144A.

*Internode*.—About 21 nodes per stem below flowers, average internode length about 4.1 cm of unpinched plant below flowers.

*Internode color*.—Same as surrounding stem.

Foliage description: Alternate; coarsely and irregularly dentate; apex and side lobes acute; base rounded; glabrous; deeply cleft nearly to petiole, typically tri-lobed; slightly lustrous adaxial surface, matte abaxial surface; leave blades to about 16.0 cm long and about 15.0 cm across, average leaf blade size 14.0 cm long and 10.0 cm wide; no fragrance detected; incisions on leaf margin few, typically three lobed;

*Foliage color*.—Mature adaxial between RHS 139A and RHS 137A; mature abaxial nearest RHS 137B; young adaxial between RHS 138A and RHS 146A; young abaxial between RHS 137B and 137C.

*Veins*.—Palmate; lustrous; ridged on abaxial.

*Vein color*.—Adaxial proximally between RHS N144A and RHS 152D; abaxial nearest RHS 145A.

*Petioles*.—Mostly terete, slightly flattened on adaxial side; glaucous; glabrous; to about 7.0 cm long and 5.0 mm diameter at base, average size about 4.7 cm long and 6.0 mm wide below leaf and 4.0 mm wide at base.

*Petiole color*.—Adaxial nearest RHS 146D; abaxial nearest RHS 146D.

Flower description: Complete; actinomophic; upward to outward facing; rotate; lasting up to two days on plant; no fragrance detected;

*Buds one day prior to opening*.—Ovoid with rounded apex and bluntly rounded base; carinate at sepal fusions; about 7.5 cm long and about 3.8 cm diameter at petal base and 2.0 cm diameter about 5.0 mm from apex; sepals flaring to about 5.8 cm diameter.

*Bud color*.—Exposed petal color between RHS 27A and RHS 29C with lighter veins of nearest RHS 19D.

*Epicalyx*.—Typically 9 to 10 per flower; entire, micropuberulent, dull surface abaxial and adaxial; linear with sharply acute apex and truncate base, arcuate upwards near apex; about 3.5 cm long and base of about 3.5 mm wide.

*Epicalyx color*.—Adaxial nearest RHS 144A and abaxial nearest RHS 138A.

*Sepals*.—Five; glabrous; acute apex; fused base; margin entire, edentate; abaxial and adaxial surfaces matte; about 5.0 cm long, fused in about the basal 2.3 cm, about 2.2 cm wide at fusion, connate forming campanulate star-shaped calyx.

*Sepal color*.—Adaxial base nearest RHS 146D with distal nearest RHS 146B; abaxial more yellow than RHS 138A and more green than RHS 146B; abaxial veins nearest RHS 138A; adaxial veins same as surrounding tissue.

*Flowers*.—Solitary, about 40 per main stem without pinching; slightly cupped petals; upward and outwardly facing; average 18.5 cm across and 6.0 cm deep from center to edge of petals; larger in early part of flowering season; with lustrous deep red eye about 5.2 cm across; persist for a one to two days; effective for at least 9 weeks beginning early August and lasting until frost; no detectable fragrance.

*Petals*.—Five; glabrous, translucent; adnate to the androecium to form a column, imbricate to about 100% overlapping at widest part (petals overlapping completely to the petals on either side), palmately veined, primary and secondary veins impressed on adaxial and ribbed abaxial; shape: rounded with distinct claw and limb; margins: entire, edentate; apex: rounded; base: short claw-like; size: average about 15.50 cm across and about 12.0 cm long (larger in earlier part of flowering season); petal undulation moderate to strong.

*Petal color*.—Adaxial eye nearest RHS 53A, mid-section white, lighter than RHS 155D, outer perimeter and leading petal edge blushed with between RHS 67B and RHS 64C, veins white, lighter than RHS 155D extending nearly to margin; abaxial basal 2.0 cm nearest RHS 155D, mid-section white, lighter than RHS 155D, edge blushed between RHS 67B and RHS 64C; color of petal perimeter and leading petal edge more intense with flowers produced in cooler conditions.

*Gynoecium*.—Single; partially enclosed in column. Column: glabrous except base micro-puberulent, lustrous; about 4.0 cm long and about 10.0 mm wide at base. Column color: nearest RHS 155D. Style: micro-puberulent in region about column; protruding from column about 13.0 mm and split in distal about 11.0 mm into typically five branches; about 4.8 cm long and branch diameter about 1.5 mm; color nearest RHS 155D. Stigma: typically five; globose, puberulent, about 3.5 mm in diameter; color nearest RHS 1D. Ovary: superior, about 8.0 mm across at base and about 7.5 mm tall; acute apex; color between RHS 145B and RHS 145C.

*Androecium*.—Filaments: numerous, about 120; about 7.0 mm long and about 0.3 mm diameter; attached along nearly the entire length of column; color nearest RHS 155D. Anthers: reniform; dorsifixed; about 2.5 mm long and 2.5 mm across and about 0.5 mm thick; color nearest RHS 11D. Pollen: abundant, globose, less than 0.1 mm long; color nearest RHS 11D.

Pedicel: Terete, glabrous, glaucous; length from base of sepal to abscission point about 2.4 cm long, from abscission point to stem node about 3.8 cm long; about 2.5 mm wide; longer on early flowers and decreasing in distal flowers; color nearest RHS 138A above and below nearest RHS 146C;

Peduncle: Terete, glabrous, glaucous; flowering in the distal 20.0 cm; color nearest RHS 146C;

Fruit: Loculicidal capsule; pubescent along inner septa, glabrous outside; globose, with abruptly acute apex; about 18.0 mm long and 16.0 mm diameter; color nearest RHS 200B when mature;

Seed: Minutely floccose, ovoid to slightly reniform; about 2.5 mm in diameter; color nearest RHS 200A;

Resistance: *Hibiscus* 'Ballet Slippers' has not displayed any pest and disease resistance beyond that typical of hardy perennial *hibiscus*. The plant grows best with plenty of moisture, but is able to tolerate some drought once established.

Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Ballet Slippers' as herein illustrated and described.

* * * * *